United States Patent [19]
Cox et al.

[11] Patent Number: 5,817,130
[45] Date of Patent: Oct. 6, 1998

[54] IMPLANTABLE CARDIAC CARDIOVERTER/ DEFIBRILLATOR WITH EMI SUPPRESSION FILTER WITH INDEPENDENT GROUND CONNECTION

[75] Inventors: Timothy John Cox; John K. Day, both of Lake Jackson, Tex.

[73] Assignee: Sulzer Intermedics Inc., Angleton, Tex.

[21] Appl. No.: 803,536

[22] Filed: Feb. 20, 1997

Related U.S. Application Data

[63] Continuation of Ser. No. 642,780, May 3, 1996, abandoned.
[51] Int. Cl.⁶ ........................................ A61N 1/39
[52] U.S. Cl. ................... 607/5; 607/36; 128/901
[58] Field of Search ............... 607/4, 5, 36, 37; 128/901

[56] References Cited

U.S. PATENT DOCUMENTS

| | | | |
|---|---|---|---|
| 3,622,918 | 11/1971 | Ito et al. | 333/79 |
| 3,718,142 | 2/1973 | Mulier | 607/901 |
| 3,872,582 | 3/1975 | Matsuoka et al. | 29/621 |
| 3,879,691 | 4/1975 | Fritz | 333/70 |
| 4,006,748 | 2/1977 | Schulman | 607/36 |
| 4,148,003 | 4/1979 | Colburn et al. | 333/181 |
| 4,247,881 | 1/1981 | Coleman | 361/302 |
| 4,306,214 | 12/1981 | Miyabayashi et al. | 338/21 |
| 4,404,972 | 9/1983 | Gordon et al. | 128/419 |

(List continued on next page.)

FOREIGN PATENT DOCUMENTS

| | | | |
|---|---|---|---|
| 0331959 | 9/1989 | European Pat. Off. | 607/36 |
| 0 776 016 A2 | 5/1997 | European Pat. Off. | H01G 4/35 |

OTHER PUBLICATIONS

S. Serge Barold et al. "Interference in Cardiac Pacemakers: Exogenous Sources," Cardiac Pacing and Electrophysiology, Third Edition (1991), pp. 608–633.

Joe Buxton, "Simple Techniques that Protect Amplifiers from High–Voltage Inputs," Sensors and Systems (May 1994), pp. 13–20.
Michael Di Martino et al., "Ferrites–Limiting What You get to What You Want," EDN Products Edition (Jun. 16, 1995).
William D. Kimmel et al., "Protecting Medical Devices from Radio–Frequency Interference," Medical Device & Diagnostic Industry, pp. 68–78.
Ivan G. Sarda et al., "Ceramic EMI Filters—A Review," Ceramic Bulletin, vol. 67, No. 4, (1988), pp. 737–746.
EPO–TEK H20E the 1–3000 GHz conductive epoxy for MIC bonding . . . .
EPO–TEK, Epoxies, Epoxy Technology, Inc.
AVX Corporation, "Transguard: Multi–Layer–Ceramic Transient Volgate Suppressors".
John Maxwell et al. "Technical Information: A Multilayer Approach to Transient Voltage Suppressors".

*Primary Examiner*—William E. Kamm
*Assistant Examiner*—Kennedy J. Schaetzle
*Attorney, Agent, or Firm*—John R. Merkling

[57] ABSTRACT

An implantable defibrillator, which may include cardioversion and pacemaker capabilities, which has EMI filters which are not susceptible to defibrillation shocks and which reduce or eliminate the effects of charging noise on sensing circuits used for continuous confirmation. A first filter capacitor is provided between a sense electrode, which may include pacing capabilities, and a ground reference within a hermetically sealed can containing a pulse/shock generator. A second filter capacitor is provided between a sensing/ pacing reference electrode, which may also be a high voltage or shock electrode, and the ground reference. In addition, there is a third filter capacitor between the ground reference and the can. Preferably, the connections of the first, second and third filter capacitors are physically as well as electrically adjacent to each other. The filter capacitors are housed in the can and in or adjacent to a feedthrough assembly which passes through the can. Most preferably, the filter capacitors are discoidal capacitors mounted in or adjacent to the feedthrough.

31 Claims, 4 Drawing Sheets

U.S. PATENT DOCUMENTS

| | | | |
|---|---|---|---|
| 4,424,551 | 1/1984 | Stevenson et al. | 361/302 |
| 4,745,923 | 5/1988 | Winstrom | 128/419 |
| 4,796,630 | 1/1989 | Regna | 128/419 |
| 4,800,883 | 1/1989 | Winstrom | 128/419 |
| 4,842,352 | 6/1989 | Sasaki et al. | 336/83 |
| 4,860,750 | 8/1989 | Frey et al. | 128/419 |
| 4,880,005 | 11/1989 | Pless et al. | 128/419 |
| 4,940,429 | 7/1990 | Chambers et al. | 439/608 |
| 5,032,809 | 7/1991 | Chambers et al. | 333/183 |
| 5,134,500 | 7/1992 | Rutt | 361/321 |
| 5,177,663 | 1/1993 | Ingleson et al. | 361/321 |
| 5,234,641 | 8/1993 | Rutt | 264/61 |
| 5,235,310 | 8/1993 | Cowman et al. | 338/21 |
| 5,274,346 | 12/1993 | Izu et al. | 333/184 |
| 5,287,076 | 2/1994 | Johnescu et al. | 333/182 |
| 5,333,095 | 7/1994 | Stevenson et al. | 361/302 |
| 5,369,390 | 11/1994 | Lin et al. | 338/21 |
| 5,406,444 | 4/1995 | Selfried et al. | 361/302 |
| 5,620,476 | 4/1997 | Truex et al. | 607/36 |

IMPLANTABLE CARDIAC CARDIOVERTER/ DEFIBRILLATOR WITH EMI SUPPRESSION FILTER WITH INDEPENDENT GROUND CONNECTION

This application is a continuation of application Ser. No. 08/642,780 filed on May 3, 1996, now abandoned.

FIELD OF OUR INVENTION

Our invention is directed towards an implantable biomedical device such as a cardiac cardioverter-defibrillator, incorporating an output regulating circuit for controlling energy applied to the heart and a sensing circuit for detecting electrical conditions in the heart, and particularly to filters for suppressing electromagnetic interference (EMI) and the effects of defibrillation shocks.

BACKGROUND OF OUR INVENTION

The basic implantable cardioverter/defibrillator system consists of at least one electrode attached to the heart and connected by a flexible lead to a shock or pulse generator. This generator is a combination of a power source and the microelectronics required for the system to perform its intended function. An implantable cardioverter/defibrillator may also include a pacemaker to treat bradycardia. Many cardioverter/defibrillators in current use incorporate circuits and antennae to communicate non-invasively with external instruments called programmers. Implantable cardioverters/ defibrillators have the capability of correcting dangerous arrhythmias and fibrillation by applying selected stimulation patterns or high energy shocks. High energy shocks are used primarily to correct life-threatening fibrillations by essentially stopping the heart and allowing an appropriate rhythm to re-establish itself.

To achieve reversion to an organized rhythm, it is generally believed that the heart should receive an effective amount of electrical energy, equal to or exceeding a threshold energy. The threshold energy may vary from patient to patient. Consequently, a physician will customarily perform certain tests when implanting a defibrillator and will select an energy level for defibrillating shocks. Implantable defibrillators are configured to deliver electrical energy by controlling the voltage on or applied from output capacitors.

Implantable medical devices such as pacemakers, defibrillators, and other implantable pulse generators generally comprise one or more electrical leads in electrical communication with the pulse generator which emanate from the housing and typically terminate at a distal location within the patient. The leads transmit electrical signals to and from the device and, as such, are fabricated having a conductor made from a metal alloy to enable good conductivity. Because of their conductive properties, these leads effectively act as an antenna and thus tend to conduct unwanted electromagnetic interference (EMI) signals. These EMI signals may be transmitted to the medical device and interfere with normal operations. Sources of EMI signals are prevalent and include, for example, radio and TV transmitters, cellular telephones, medical electrosurgical equipment, microwave devices, welding equipment, security and surveillance systems, and other sources of radio frequency interference (RFI). In implantable cardioverter/ defibrillators, charging and delivery of a defibrillating shock can cause EMI which adversely affects the sensing circuits or the operation of the device.

Two basic approaches are employed to reduce the effects of unwanted EMI on implantable medical device operations. In the first approach, the medical device is enclosed in a metallic housing or shield which may be conductively connected to a ground reference of the device. In the second approach, a filtering circuit attenuates potential EMI before it reaches the circuitry of the medical device. The two approaches may be used sepeartely or combined.

Presently, multilayer ceramic type capacitors and, in particular, discoidal capacitors are recognized as an effective alternative for filtering EMI. In a typical construction, these discoidal capacitors form part of a feedthrough filter assembly, which admits patient connections through the hermetic barrier of the device. The feedthrough assembly includes a metallic ferrule connected to the capacitor and a terminal pin hermetically supported from and extending through the ferrule. The metallic ferrule is connected to and hermetically sealed with the medical device. Typically, the discoidal capacitor has two separate electrode plate sets which are embedded within a dielectric substrate. One set of the electrode plates is electrically coupled to the terminal pin. This pin is electrically connected at one end to the medical device circuitry and at another end to the lead used to transmit the desired electrical signals to and from the patient. The other set of electrode plates is electrically coupled to a cylindrically shaped ferrule which, in turn, is welded to the housing of the medical device. Generally, the ferrule consists of a conductive material and may have an insulating material disposed along an inner portion of the outer conductive surface. This insulating material is used to support the terminal pin and maintain it in nonconductive relation with the housing of the medical device.

During signal transmission, the discoidal capacitor permits passage of relatively low frequency signals along the lead, through the terminal pin, and to the medical device. Higher frequencies, representative of the spectrum of unwanted EMI, however, are shunted to the housing of the medical device by the capacitor and not permitted to pass into the medical device. As a consequence, interfering signals which could otherwise adversely affect the performance of the device are filtered as they enter the medical device.

Discoidal capacitors, as well as other multilayer ceramic capacitors, are formed of multiple layers of alternating ceramic and metallic materials. Generally, the multilayer ceramics are available in several different dielectrics and the choice of material depends on the desired capacitance volume efficiency and the operating temperature range. Ceramic capacitors of this nature, however, primarily serve to filter EMI and not protect against voltage transients and surges. For further information regarding discoidal and multilayer capacitors, reference should be made to U.S. Pat. No. 5,333,095 by Stevenson et al., issued Jul. 26, 1994, entitled "Feedthrough Filter Capacitor Assembly for Human Implant", and Ivan G. Sarda and William H. Payne, "Ceramic EMI Filters—A Review," *Ceramic Bulletin,* Vol. 67, No. 4 (1988), pp. 737–746.

Implantable defibrillators usually produce high voltage, high energy shocks by charging large capacitors. It takes a certain amount of time, depending on the condition of the batteries and other factors, to charge these high voltage capacitors. During this interval, it is possible that the heart may spontaneously revert to a normal sinus rhythm. Since a defibrillation shock is both painful and potentially dangerous, it is desirable to avoid delivering unnecessary shocks. To do this, implantable defibrillators are programmed to continue to monitor the electrical condition of the heart during a capacitor charging interval. If normal sinus rhythm is detected, charging is interrupted and a shock is not delivered. This is sometimes referred to as "continuous confirmation," meaning that the existence of a life-threatening tachycardia or fibrillation is constantly detected. It has been observed, however, that the process of charging the high voltage capacitors can be so electrically noisy that the heart's electrical signal cannot be reliably detected. This noise appears as internally-generated EMI, transmitted from high voltage leads or electrodes to a sensing circuit. It is desirable, therefore, to reduce or eliminate this noise so that the sensing circuit can more readily detect the heart's electrical signals.

Certain implantable cardioverter/defibrillators have been developed which deliver shocks between an electrode mounted on a lead, preferably an endocardial lead, and a conductive part of the hermetically sealed case or can containing the pulse generator. This is sometimes referred to as a "hot can" and is analogous to so-called unipolar operation of a pacemaker, wherein a stimulating pulse is delivered between an electrode and a pacemaker can. The magnitude of a shock is, of course, substantially greater than a pacing pulse and presents additional difficulties. In particular, we have found that in a "hot can" implantable cardioverter/defibrillator with EMI filters, a shock waveform may be prematurely terminated by a feedback effect. This appears to be attributable to the use of at least two EMI suppressing capacitor filters, between each pace/sense electrode, which may also be a high voltage or shock electrode, and the can.

This phenomenon can be avoided by removing the EMI suppressing capacitor filters or by substantially reducing their capacitance. This, however, renders the device more susceptible to externally generated electromagnetic interference.

It is an object of our invention, therefore, to provide an implantable cardioverter/defibrillator in which the design of EMI suppressing filters is not influenced by the programmed selection of shock delivery path.

It is a further object of our invention to provide an EMI filter configuration for an implantable cardioverter/defibrillator which prevents premature termination of shock delivery.

It is another object of our invention to provide an implantable defibrillator which has continuous confirmation, but which is not susceptible to charging noise.

SUMMARY OF OUR INVENTION

We have invented an implantable defibrillator, which may include cardioversion and pacemaker capabilities, which has EMI filters which are not susceptible to defibrillation shocks and which reduce or eliminate the effects of charging noise on sensing circuits used for continuous confirmation. A first filter capacitor is provided between a sense electrode, which may include pacing capabilities, and a ground reference within a hermetically sealed can containing a pulse/shock generator. A second filter capacitor is provided between a pacing/sensing referenc electrode, which may also be a high voltage or shock electrode, and the ground reference. In addition, there is a third filter capacitor between the ground reference and the can. Preferably, the connections of the first, second and third filter capacitors are physically as well as electrically adjacent to each other. In our preferred embodiment, the filter capacitors are housed in the can and in or adjacent to a feedthrough assembly which passes through the can. Most preferably, the filter capacitors are discoidal capacitors mounted in or adjacent to the feedthrough.

We will now describe our preferred embodiment of our invention, in connection with the accompanying drawings.

DESCRIPTION OF OUR PREFERRED INVENTION

Figure 1:
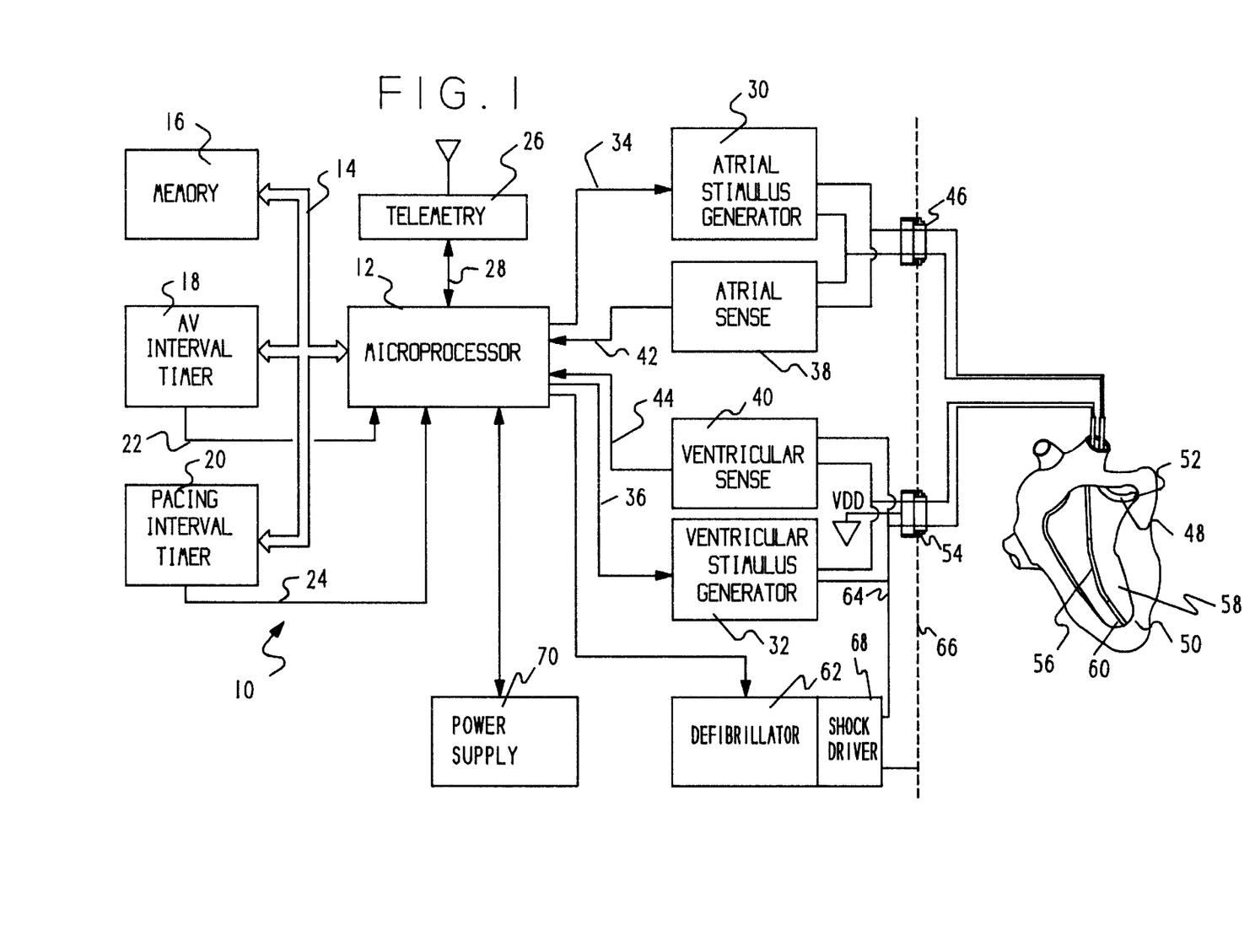
FIG. 1 is a block diagram of an implantable pacemaker/defibrillator.

FIG. 1 is a block diagram illustrating a rate adaptive pacemaker/defibrillator 10 according to our invention. A microprocessor 12 preferably provides pacemaker control and computational facilities. It will be appreciated that other forms of circuitry, such as analog or discrete digital circuitry can be used in place of microprocessor 12. However, a microprocessor is preferred for its miniature size and its flexibility, both of which are of critical importance in the implantable systems in which it is envisioned the invention will find use. A particularly energy efficient microprocessor which is designed specifically for use with implantable medical devices is fully described in Gordon, et al., U.S. Pat. No. 4,404,972, which is also assigned to our assignee and the disclosure thereof is incorporated herein by reference.

The microprocessor 12 has input/output ports connected in a conventional manner via bidirectional bus 14 to a memory 16, an A-V interval timer 18, and a pacing interval timer 20. In addition, the A-V interval timer 18 and pacing interval timer 20 each has an output connected individually to a corresponding input port of the microprocessor 12 by lines 22 and 24 respectively.

Memory 16 preferably includes both ROM and RAM. The microprocessor 12 may also contain additional ROM and RAM as described in the Gordon, et al. U.S. Pat. No. 4,404,972. The pacemaker operating routine is stored in ROM. The RAM stores various programmable parameters and variables.

The A-V and pacing interval timers 18 and 20 may be external to the microprocessor 12, as illustrated, or internal thereto, as described in the Gordon, et al. U.S. Pat. No. 4,404,972. The timers 18, 20 are suitable conventional up or down counters of the type that are initially loaded with a count value and count up to or down from the value and output a roll-over bit upon completing the programmed count. The initial count value is loaded into the timers 18, 20 on bus 14 and the respective roll-over bits are output to the microprocessor 12 on lines 22, 24.

The microprocessor 12 preferably also has an input/output port connected to a telemetry interface 26 by line 28. The defibrillator, when implanted, is thus able to receive pacing, arrhythmia therapy, and rate control parameters from an external programmer and send data to an external receiver if desired. Many suitable telemetry systems are known to those skilled in the art. One such system and encoding arrangement is described in Armstrong and Cox, U.S. Pat. No. 5,383,912 which is also assigned to our assignee. That description is incorporated herein by reference.

The microprocessor output ports are connected to inputs of an atrial stimulus pulse generator 30 and a ventricle stimulus pulse generator 32 by control lines 34 and 36 respectively. The microprocessor 12 transmits pulse parameter data, such as amplitude and width, as well as enable/disable and pulse initiation codes to the generators 30, 32 on the respective control lines. The microprocessor 12 also has input ports connected to outputs of an atrial sense amplifier 38 and a ventricular sense amplifier 40 by lines 42 and 44 respectively. The atrial and ventricular sense amplifiers 38, 40 detect electrical conditions in the heart including fibrillation and occurrences of P-waves and R-waves. The atrial sense amplifier 38 outputs a signal on line 42 to the microprocessor 12 when it detects a P-wave. This signal is latched to the microprocessor 12 input port by a conventional latch (not shown). The ventricular sense amplifier 40 outputs a signal on line 44 to the microprocessor 12 when it detects an R-wave. This signal is also latched to the microprocessor 12 input port by a conventional latch (not shown).

The input of the atrial sense amplifier 38 and the output of the atrial stimulus pulse generator 30 are connected by conductors through a first EMI filtering feedthrough 46, and through a conventional first lead 48 to a patient's heart 50. Lead 48 is inserted into the patient's heart 50 intravenously or in any other suitable manner. The lead 48 has an electrically conductive pacing/sensing tip 52 or tip and ring at its distal end which is electrically connected to the conductors in lead 48. The pacing/sensing tip 52 is preferably lodged in the right atrium. The input of the ventricular sense amplifier 40 and the output of the ventricular stimulus pulse generator 32 are connected by conductors through a second EMI filtering feedthrough 54. The conductors pass through a conventional second lead 56 which is inserted intravenously or otherwise in the right ventricle 58 of the heart 50. The second lead 56 has an electrically conductive pacing/sensing tip 60 or tip and ring at its distal end. The pacing/sensing tip 60 is electrically connected to the conductors in second lead 56. The pacing/sensing tip 60 is preferably lodged on the wall of the right ventricle 58.

The conductors conduct the stimulus pulses generated by the atrial and ventricular stimulus pulse generators 30, 32 to the pacing/sensing tips 52, 60. The pacing/sensing tips 52, 60 and corresponding conductors also conduct cardiac electrical signals sensed in the right atrium and right ventricle to the atrial and ventricular amplifiers, 38, 40 respectively. The sense amplifiers 38, 40 enhance the electrical signals. In the preferred embodiments of our invention, the amplifiers 38, 40 have an automatic gain control feature, as described in U.S. Pat. No. 4,903,699 to Baker, et al. That application is assigned to the same assignee as our present invention, and the disclosure thereof is incorporated herein by reference.

The implantable cardiac stimulator 10 also has a defibrillator circuit 62. If fibrillation is detected through the atrial or ventricular sense amplifiers 38, 40, a high energy shock can be delivered through defibrillation lead 64 and electrode 56. Detection algorithms for detection of tachycardias and fibrillation are described in Pless, et al., U.S. Pat. No. 4,880,005, incorporated herein by reference. Although an endocardial electrode and use of the conductive part of the can or case are suggested by the drawing, patch-type epicardial electrodes for defibrillation are also known. The shock is controlled by a shock driver circuit 68, which will be more particularly described hereafter. All of the aforementioned components are powered by a power supply 70. The power supply 70 may comprise either standard or rechargeable batteries or both, which may be dedicated to the operation of different parts of the stimulator 10.

Figure 2:
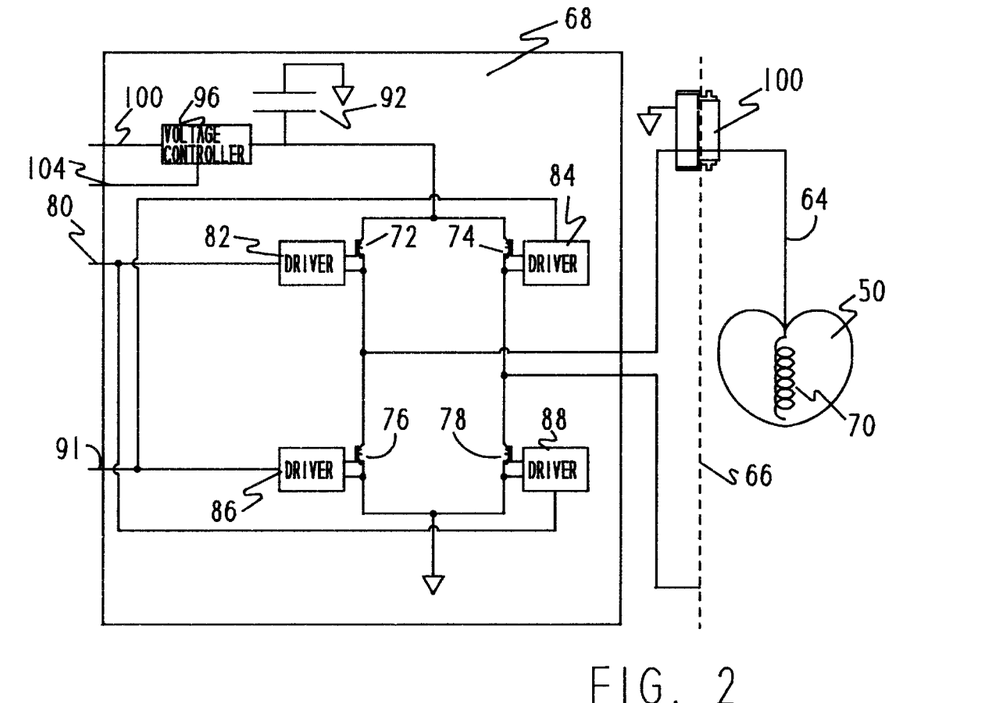
FIG. 2 is a block diagram of an output circuit for use in the defibrillator of FIG. 1.

In the preferred embodiment of our invention, we consider it desirable to produce multi-phasic shocks for defibrillation through the shock driver 68. Circuitry particularly well adapted for producing such wave forms is described in detail in U.S. Pat. No. 4,800,883 to Winstrom, the disclosure of which is incorporated herein by reference. Circuitry for the shock driver 68 is shown with greater particularity in FIG. 2. FIG. 2 illustrates the shock driver 68 connected to the patient's heart 50 through the lead 64 and electrode 56 and through the can 66. To produce a biphasic wave form, a bank of four three-terminal semiconductor switches 72, 74, 76, 78, such as insulated gate bipolar transistor (IGBT) switches, may be employed. It will be understood, however, that our invention can be employed with monophasic pulse generators and with pulse generators incorporating multiphasic stimulation. The switches 72, 74, 76, 78 are controlled by drivers 82, 84, 86, 88 respectively. The drivers 82, 84, 86, 88 are controlled by command pulses from the microprocessor 12 through control lines 80 and 91, as will be more particularly described below. The energy to produce biphasic defibrillating shocks is supplied from high voltage capacitor 92. High voltage capacitor 92 is connected to switches 72 and 74, and current therefrom returns via switches 76 or 78. The first lead 64 is connected between switches 72 and 76 while the second lead 66 is connected between switches 74 and 78.

The amount of energy delivered to the heart is dependent upon the voltage on the high voltage capacitor. The voltage appearing on the capacitor 92 is controlled by voltage controller 96 which is connected to a source of power such as the battery or power supply 70 through line 100. The voltage controller 96 is controlled through a line 104 from the microprocessor 12. This configuration is described in more detail in the Winstrom patent mentioned above. In the configuration shown, to produce a unidirectional current pulse through the heart 50, the microprocessor 12 issues a command along line 80 to drivers 82 and 88, closing switches 72 and 78. Both before and after the command, all switches are normally opened. To produce an opposite current, the microprocessor 12 issues a command on line 90, closing switches 84 and 86 and directing the current flow in the opposite direction through the heart 50.

Figure 3:
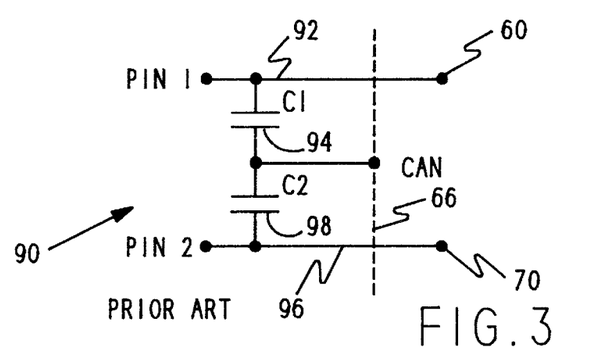
FIG. 3 is a schematic diagram of a prior art EMI filter circuit.

We will now describe the EMI filter according to our invention. A prior art EMI filter 90 is illustrated in FIG. 3. Such a filter 90 might be comprised of discrete components, or incorporated into a set of discoidal capacitors. Such discoidal capacitors might be mounted in a feedthrough such as feedthrough 54, or adjacent the feedthrough, as described in Stephenson et al. U.S. Pat. No. 5,333,095. Fundamentally, an EMI filter 90 comprises a lead 92 which would pass through a desired case such as the can 66 to provide an electrical connection through the can 66. The lead 92 might, for example, be connected to the ventricular sense circuit 40 and the ventricular stimulus generator 32 within the can at pin 1 and to the tip electrode 60 outside of the can. A first capacitor 94 is connected from the lead 92 to the can 66 to provide a high frequency path for EMI. Multiple leads and capacitors could be provided in a single configuration or at a single feedthrough. For example, as shown in FIG. 3, an additional lead 96 could be provided within an associated capacitor 98 connected from the additional lead 96 to the can 66. Pin 2 of lead 96 might be connected, for example, to the shock driver 68 within the can and to the endocardial electrode 70 outside of the can.

In an implantable cardioverter defibrillator, charging noise is generated during the process of charging the high voltage capacitors in the defibrillator 62 prior to shock delivery. Charging noise may be present as an electric field coupling from the can or by induction of eddy currents. This sometimes occurs when a "hot can" electrode has been introduced into the shock delivery pathway, that is, when the can 66 is used as one of the electrodes. We have found that the prior art connection of the C1 and C2 capacitors 94, 98 respectively, directly to the can 66 can cause an inappropriate sensing during the charging cycle and premature termination of a can-delivered shock. Even if two or more defibrillation electrodes remote from the can are used, charging noise can still prevent a sensing circuit from detecting the electrical condition of the heart, if continuous confirmation of the life-threatening condition is attempted. These situations are avoided by the configuration of our invention illustrated in FIG. 4.

Figure 4:
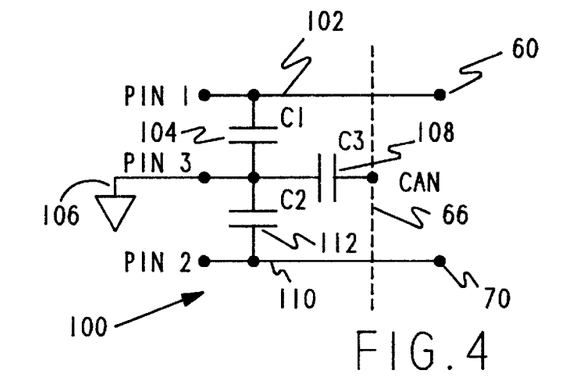
FIG. 4 is a schematic diagram of an EMI filter circuit according to our invention.
Figure 5:
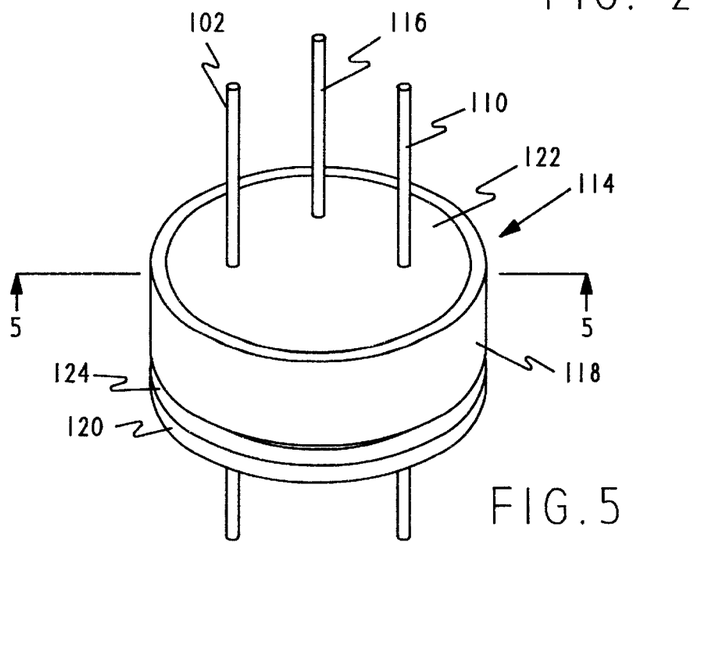
FIG. 5 is a perspective view of a combined hermetic feedthrough and filter circuit according to our invention.

FIG. 4 illustrates an EMI filter 100 according to our invention. The EMI filter 100 comprises at least one lead 102, configured to pass through the can 66. As before, this lead 102 might be connected within the can at pin 1 to the ventricular sense circuit 40 and the ventricular stimulus generator 32. Outside the can 66 the lead 102 might be connected to the ventricular tip electrode 60. A shunt capacitor 104 is provided similar to the capacitor 94 described above. However, instead of being connected to the can 66, this capacitor is connected directly to the internal system ground 106. A C3 capacitor 108 is connected between the common contact of the C1 capacitor 104 and of the system ground 106 and the can 66. In our preferred embodiment, the capacitance of the C1 capacitor and the C3 capacitor are approximately equal. Charging noise is generally within the frequency range of 100 kHz to 200 kHz. Consequently, the C1 capacitor is chosen to easily pass frequencies higher than 100 kHz. These frequencies are passed directly to the system ground since it passes through but a single capacitor. This adequately diminishes the effect of charging noise on the circuit and prevents improper sensing. On the other hand, external EMI generally consists of frequencies in excess of 1 MHz. These frequencies are passed easily through the capacitor C1 and C3 in series and are diverted to the can. External EMI entering either from the tip electrode 60 or the endocardial defibrillation electrode 70 needs to be attenuated before it can be demodulated by the rectifying properties of semi-conductor junctions. This is done by shunting the EMI currents back to the can which acts as a Faraday Cage for the device. The C3 capacitor 108 provides a low impedance path from the ground reference to the can.

Multiple leads may be provided through the can, either electrically adjacent, or both electrically and physically adjacent one another. For example, an additional lead 110 could be provided to connect to the endocardial defibrillation electrode 70 and through pin 2 to the shock driver 68. A C2 capacitor 112 is connected from the lead 10 to the system ground 106 and to the C3 capacitor 108.

The EMI filter 100 of our invention may be provided as separate components connected to a standard feedthrough. However, our preferred embodiment is to construct a feedthrough and EMI filter as a common feedthrough structure 114 as illustrated in perspective view in FIG. 4. The feedthrough structure 114 comprises the leads 102 and 110 described above and a system ground connection 116 for connection to the system ground 106. The leads 102, 110 and 116 are embedded in a feedthrough 118 having a metal ferule 120 for connection to the can 66 which houses a capacitor structure 122. The capacitor structure 122 may be constructed in a variety of ways, as we will now explain.

Figure 6:
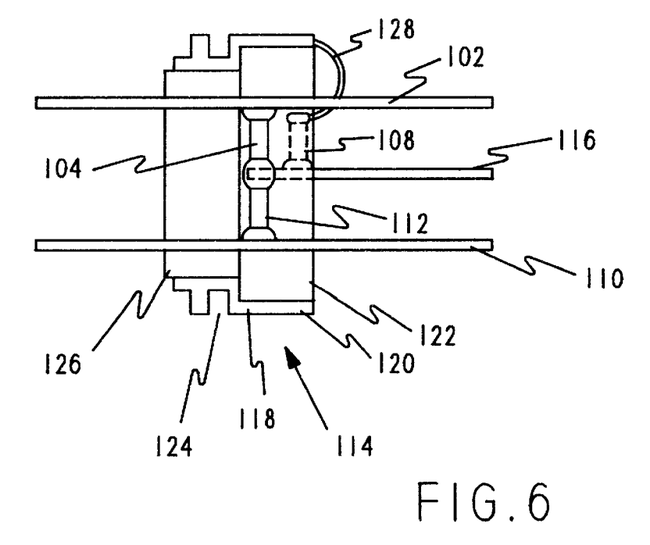
FIG. 6 is a through section plan view of a first embodiment of the feedthrough and filter circuit of FIG. 5.

One embodiment is shown in FIG. 6, which represents a plane through section of the feedthrough system 114 of FIG. 4. As seen in FIG. 6, the metal ferrule 120 of the feedthrough 118 has a circumferential groove 124 for receiving the can 66. A hermetic seal 126 plugs one end of the feedthrough 118 around the leads 102 and 110. Such hermetic seals are known in the art, and are described, for example, in U.S. Pat. Nos. 3,920,888 and 4,678,868. The capacitor assembly 122 comprises chip capacitors employed for the capacitors 104, 112 and 108. The shunt capacitor 108 is connected by a jumper 128 to the metal ferrule 120. Alternatively, the jumper 128 could be connected directly to the can 66.

Figure 7:
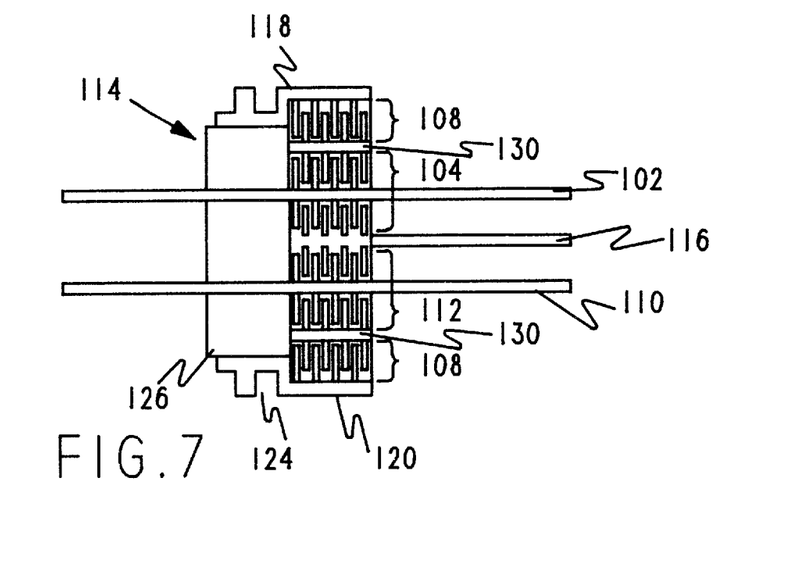
FIG. 7 is a through section plan view of a second embodiment of the feedthrough and filter circuit of FIG. 5.

An alternative construction comprised of discoidal capacitors is illustrated in through section in FIG. 7. As in the embodiment of FIG. 6, the leads 102, 110 and 116 and the metal ferrule 120 and hermetic plug 126 are substantially as described above, and perform the same functions. Instead of the chip capacitors, however, the capacitors 104, 108 and 112 are comprised of discoidal capacitors. In particular, the ground line 116 which is intended to be connected to system ground 106 is connected to an annular ring conductor 130. Plates on the outside of this ring 130 interleave with plates connected to the ferrule 120, thus forming the shunt capacitor 108 which connects to the can through the ferrule 120. On the inside of the annular conductor 130, additional plates interleave with plates connected to the lines 102 and 110 to form capacitors 104 and 112 respectively.

Figure 8:
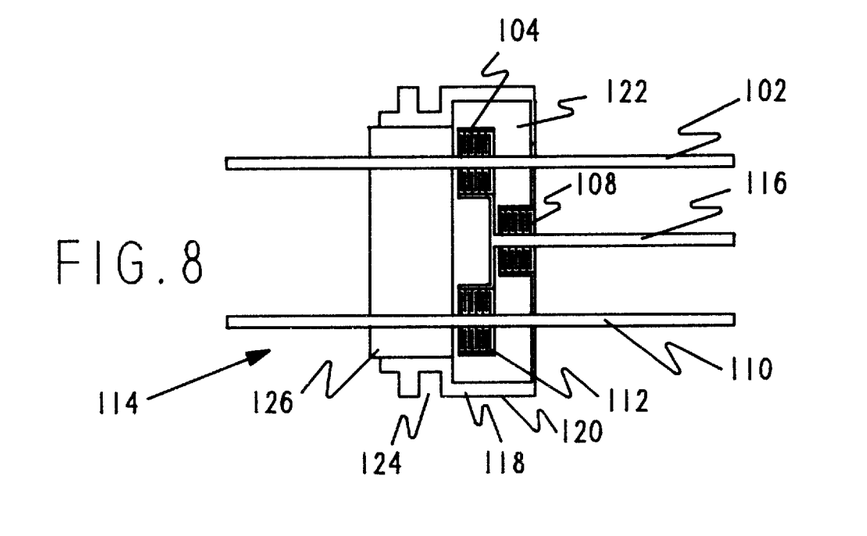
FIG. 8 is a through section plan view of a third embodiment of the feedthrough and filter circuit of FIG. 5.

A third embodiment is illustrated in through section in FIG. 8. As in FIGS. 6 and 7, like numerals indicate like parts. In this embodiment, however, the capacitors 104, 108 and 112 are formed as individual stacked discoidal capacitors formed adjacent their respective leads 102, 116 and 110.

Each of the embodiments of FIGS. 6, 7 and 8 are shown with the capacitor structure 102 contained within the ferrule 120 of the feedthrough 118. However, our invention could also be implemented using discoidal capacitors attached around the ferrule, as shown, for example, in Stephenson et al. U.S. Pat. No. 5,333,095.

While a preferred embodiment of our invention has been described above, it will be apparent to those skilled in the art from consideration of the disclosure herein that various modifications could be implemented without departing from the principles of our invention. Accordingly, it is intended that the scope of our invention be limited only by the appended claims.

We claim as our invention:

1. An implantable defibrillator comprising
   a hermetically sealed can;
   circuit means for detecting the condition of the heart of a patient;
   means responsive to said circuit means for producing a defibrillation shock;
   a battery electrically connected to said circuit means and to said means for producing a defibrillation shock, said battery having electrical ground producing means;
   means for connecting said means for producing a defibrillation shock to a first defibrillation electrode;
   means for connecting said means for producing a defibrillation shock to a second defibrillation electrode; and
   a first EMI filter connecting said shock producing means and said means for connecting to first defibrillation electrode, said first EMI filter comprising an electrical conductor connecting said shock producing means and said means for connecting to said first defibrillation electrode;
a first capacitor connecting said electrical conductor to said electrical ground producing means; and
a second capacitor connecting said electrical ground producing means and said first capacitor to said can.

2. The implantable defibrillator according to claim 1 wherein said means for connecting to a second defibrillation electrode is connected to said can and wherein at least a portion of said can is a defibrillation electrode.

3. The implantable defibrillator according to claim 1 wherein at least one of said first and second capacitors is a chip capacitor.

4. The implantable defibrillator according to claim 3 further comprising an hermetically sealed feedthrough and wherein said EMI filter is mounted adjacent said feedthrough.

5. The implantable defibrillator according to claim 4 wherein said means for connecting to a second defibrillation electrode is connected to said can and wherein at least a portion of said can is a defibrillation electrode.

6. The implantable defibrillator according to claim 1 wherein at least one of said first and second capacitors is a discoidal capacitor.

7. The implantable defibrillator according to claim 6 further comprising an hermetically sealed feedthrough and wherein said EMI filter is mounted adjacent said feedthrough.

8. The implantable defibrillator according to claim 7 wherein said means for connecting to a second defibrillation electrode is connected to said can and wherein at least a portion of said can is a defibrillation electrode.

9. The implantable defibrillator according to claim 1 further comprising
a second EMI filter connecting said circuit means and said means for connecting a defibrillating lead, said second EMI filter comprising
a second electrical conductor connecting said circuit means and said means for connecting a defibrillating lead;
a third capacitor connecting said second electrical conductor to said electrical ground producing means; and
said second capacitor connecting said electrical ground producing means and said third capacitor to said can.

10. The implantable defibrillator according to claim 9 wherein at least one of said first, second and third capacitors is a chip capacitor.

11. The implantable defibrillator according to claim 10 further comprising an hermetically sealed feedthrough and wherein said EMI filter is mounted adjacent said feedthrough.

12. The implantable defibrillator according to claim 11 wherein said means for connecting to a second defibrillation electrode is connected to said can and wherein at least a portion of said can is a defibrillation electrode.

13. The implantable defibrillator according to claim 9 wherein at least one of said first, second and third capacitors is a discoidal capacitor.

14. The implantable defibrillator according to claim 13 further comprising an hermetically sealed feedthrough and wherein said EMI filter is mounted adjacent said feedthrough.

15. The implantable defibrillator according to claim 14 wherein said means for connecting to a second defibrillation electrode is connected to said can and wherein at least a portion of said can is a defibrillation electrode.

16. An implantable defibrillator comprising
a hermetically sealed can, at least part of said can being a defibrillation electrode;
means for connecting a defibrillation lead to said implantable defibrillator;
circuit means for detecting the condition of the heart of a patient;
means responsive to said circuit means for producing a defibrillation shock;
a battery electrically connected to said circuit means and to said means for producing a defibrillation shock, said battery having electrical ground producing means; and
a first EMI filter connecting said circuit means and said means for connecting a defibrillating lead, said first EMI filter comprising
an electrical conductor connecting said circuit means and said means for connecting a defibrillating lead;
a first capacitor connecting said electrical conductor to said electrical ground producing means; and
a second capacitor connecting said electrical ground producing means and said first capacitor to said can.

17. The implantable defibrillator according to claim 16 wherein at least one of said first and second capacitors is a chip capacitor.

18. The implantable defibrillator according to claim 17 further comprising a hermetically sealed feedthrough and wherein said EMI filter is mounted adjacent said feedthrough.

19. The implantable defibrillator according to claim 16 wherein at least one of said first and second capacitors is a discoidal capacitor.

20. The implantable defibrillator according to claim 19 further comprising a hermetically sealed feedthrough and wherein said EMI filter is mounted adjacent said feedthrough.

21. An EMI filter for an implantable defibrillator, said EMI filter comprising
a hermetically sealed feedthrough, said feedthrough having an electrically conductive casing;
a first electrical conductor passing in sealed relationship through said feedthrough;
a first capacitor having a first terminal and a second terminal, said first capacitor being connected to said first electrical conductor at said first terminal of said first capacitor;
a second conductor connected to said first capacitor at said second terminal of said first capacitor; and
a second capacitor having a first terminal and a second terminal, said second capacitor being connected to said second conductor at said first terminal of said second capacitor and to said electrically conductive casing at said second terminal of said second capacitor.

22. The EMI filter according to claim 21 wherein at least one of said first and second capacitors is a chip capacitor.

23. The EMI filter according to claim 21 wherein at least one of said first and second capacitors is a discoidal capacitor.

24. The EMI filter according to claim 21, said EMI filter further comprising
a third electrical conductor passing in sealed relationship though said feedthrough; and
a third capacitor having a first terminal and a second terminal, said third capacitor being connected to said third electrical conductor at said first terminal of said first capacitor; being connected to said second conductor at said second terminal of said third capacitor.

25. The EMI filter according to claim 24 wherein at least one of said first, second and third capacitors is a chip capacitor.

26. The EMI filter according to claim 24 wherein at least one of said first, second and third capacitors is a discoidal capacitor.

27. An implantable defibrillator comprising a hermetically sealed can;

circuit means for detecting the condition of the heart of a patient;

means responsive to said circuit means for producing a defibrillation shock;

a battery electrically connected to said circuit means and to said means for producing a defibrillation shock, said battery having electrical ground producing means;

means for connecting said means for producing a defibrillation shock to a first defibrillation electrode;

means for connecting said means for producing a defibrillation shock to a second defibrillation electrode; and a first EMI filter connecting said shock producing means and said means for connecting to said first defibrillation electrode, said first EMI filter comprising an electrical conductor connecting said shock producing means and said means for connecting to said first defibrillation electrode;

means connected to said electrical conductor for conducting EMI having a first predetermined frequency range to said electrical ground producing means; and means connected to said electrical conductor for conducting EMI having a second predetermined frequency range to said can.

28. An implantable defibrillator comprising a hermetically sealed can;

circuit means for detecting the condition of the heart of a patient;

means responsive to said circuit means for producing a defibrillation shock;

a battery electrically connected to said circuit means and to said means for producing a defibrillation shock, said battery having electrical ground producing means;

means for connecting said circuit means for detecting the condition of the heart of a patient to a first electrode; and a first EMI filter connecting said circuit means and said means for connecting to said first electrode, said first EMI filter comprising an electrical conductor connecting said circuit means and said means for connecting to said first electrode;

means connected to said electrical conductor for conducting EMI having a first predetermined frequency range to said electrical ground producing means; and means connected to said electrical conductor for conducting EMI having a second predetermined frequency range to said can.

29. The implantable defibrillator according to claim 28 further comprising means for connecting said circuit means for detecting the condition of the heart of a patient to a second electrode; and a second EMI filter connecting said circuit means and said means for connecting to said second electrode, said second EMI filter comprising an electrical conductor connecting said circuit means and said means for connecting to said second electrode;

means connected to said electrical conductor for conducting EMI having a third predetermined frequency range to said electrical ground producing means; and means connected to said electrical conductor for conducting EMI having a fourth predetermined frequency range to said can.

30. The implantable defibrillator according to claim 29 wherein said second predetermined frequency range is substantially equal to said fourth predetermined frequency range.

31. The implantable defibrillator according to claim 29 further comprising means for connecting said means for producing a defibrillation shock to said first defibrillation electrode; and wherein said second EMI filter further connects said shock producing means and said means for connecting to said first defibrillation electrode.

* * * * *